US010143441B2

(12) United States Patent
Yoshioka et al.

(10) Patent No.: US 10,143,441 B2
(45) Date of Patent: Dec. 4, 2018

(54) ULTRASONIC PROBE

(71) Applicant: SOCIONEXT INC., Yokohama-shi, Kanagawa (JP)

(72) Inventors: Masato Yoshioka, Yokohama (JP); Kazuyuki Kanazashi, Yokohama (JP)

(73) Assignee: Socionext Inc., Yokohama (JP)

( * ) Notice: Subject to any disclaimer, the term of this patent is extended or adjusted under 35 U.S.C. 154(b) by 0 days.

(21) Appl. No.: 15/721,228

(22) Filed: Sep. 29, 2017

(65) Prior Publication Data
US 2018/0021016 A1 Jan. 25, 2018

Related U.S. Application Data

(63) Continuation of application No. PCT/JP2016/052670, filed on Jan. 29, 2016.

(30) Foreign Application Priority Data

Apr. 17, 2015 (JP) ................. 2015-085196

(51) Int. Cl.
*A61B 8/00* (2006.01)
*A61B 8/14* (2006.01)
(Continued)

(52) U.S. Cl.
CPC ............. *A61B 8/4444* (2013.01); *A61B 8/14* (2013.01); *A61B 8/4494* (2013.01);
(Continued)

(58) Field of Classification Search
CPC ....... A61B 8/4444; A61B 8/14; A61B 8/4494; G01N 27/4148; G01N 29/34; G01N 29/36;
(Continued)

(56) References Cited

U.S. PATENT DOCUMENTS 3,727,216 A * 4/1973 Antonio ................. G01S 13/56
340/554
6,142,946 A 11/2000 Hwang et al.
(Continued)

FOREIGN PATENT DOCUMENTS

JP    H11177015 A    7/1999
JP    11-274672 A    10/1999
(Continued)

OTHER PUBLICATIONS

International Search Report Written Opinion issued in related International Application No. PCT/JP2016/052670 dated May 10, 2016.

*Primary Examiner* — Bo J Peng
(74) *Attorney, Agent, or Firm* — Arent Fox LLP

(57) ABSTRACT

An ultrasonic probe includes, a transducer transmitting and receiving ultrasonic waves, and converting ultrasonic signals into voltage signals and vice versa, a first circuit configured to transmit pulse voltage signals to the transducer and receive the voltage signals from the transducer, a second circuit configured to convert the voltage signals received from the first circuit into digital values from analog values, a battery unit configured to supply electric power to the first circuit and the second circuit, and a substrate being provided with the transducer, the first circuit and the second circuit, the first circuit being disposed on a first surface of the substrate, and the second circuit being disposed on a second surface opposite to the first surface of the substrate.

8 Claims, 12 Drawing Sheets

(51) Int. Cl.

| | | |
|---|---|---|
| *G01S 7/52* | (2006.01) | |
| *G01S 15/89* | (2006.01) | |
| *H01L 27/32* | (2006.01) | |
| *H01L 23/50* | (2006.01) | |
| *H04R 25/00* | (2006.01) | |
| *G01N 27/414* | (2006.01) | |
| *G01N 29/34* | (2006.01) | |
| *G01N 29/44* | (2006.01) | |
| *G01N 29/36* | (2006.01) | |

(52) U.S. Cl.
CPC ......... *G01N 27/4148* (2013.01); *G01N 29/34* (2013.01); *G01N 29/36* (2013.01); *G01N 29/44* (2013.01); *G01S 7/52079* (2013.01); *G01S 15/8906* (2013.01); *H01L 23/50* (2013.01); *H01L 27/3297* (2013.01); *H04R 25/30* (2013.01); *G01N 2201/0693* (2013.01); *G01N 2201/123* (2013.01); *G01N 2201/125* (2013.01); *G01N 2201/1263* (2013.01); *H01L 2224/75347* (2013.01); *H01L 2224/76347* (2013.01); *H01L 2224/77347* (2013.01); *H01L 2224/78347* (2013.01); *H01L 2224/79347* (2013.01); *H04R 2225/33* (2013.01)

(58) Field of Classification Search
CPC ........... G01N 29/44; G01N 2201/0693; G01N 2201/123; G01N 2201/125; G01N 2201/1263; G01S 7/52079; G01S 15/8906; H01L 23/50; H01L 27/3297; H01L 2224/75347; H01L 2224/76347; H01L 2224/77347; H01L 2224/78347; H01L 2224/79347; H01R 25/30; H01R 2225/33

See application file for complete search history.

(56) References Cited

U.S. PATENT DOCUMENTS

| | | | |
|---|---|---|---|
| 6,530,887 | B1 | 3/2003 | Gilbert et al. |
| 8,439,840 | B1* | 5/2013 | Duffy .................... A61B 8/483 |
| | | | 600/437 |
| 2002/0012234 | A1 | 1/2002 | Harada et al. |
| 2004/0033175 | A1 | 2/2004 | Ohno et al. |
| 2010/0160785 | A1 | 6/2010 | Poland et al. |
| 2010/0168576 | A1 | 7/2010 | Poland et al. |
| 2012/0078278 | A1* | 3/2012 | Bales, Jr. ....... A61B 17/320092 |
| | | | 606/169 |
| 2014/0347954 | A1 | 11/2014 | Maurice et al. |

FOREIGN PATENT DOCUMENTS

| | | |
|---|---|---|
| JP | 2002-530142 A | 9/2002 |
| JP | 2002-530175 A | 9/2002 |
| JP | 2002-289991 A | 10/2002 |
| JP | 2003-506172 A | 2/2003 |
| JP | 2007-244580 A | 9/2007 |
| JP | 2010-528696 A | 8/2010 |
| JP | 2010-528698 A | 8/2010 |
| JP | 2010-220791 A | 10/2010 |
| JP | 2015-500117 A | 1/2015 |

* cited by examiner

ULTRASONIC PROBE

CROSS-REFERENCE TO RELATED APPLICATION

The present application is a continuation application of International Application No. PCT/JP2016/052670, filed on Jan. 29, 2016, which claims priority to Japanese Patent Application No. 2015-085196, filed on Apr. 17, 2015. The contents of these applications are incorporated herein by reference in their entirety.

FIELD

The present invention pertains to an ultrasonic probe.

BACKGROUND

There is utilized an ultrasonic diagnostic imaging apparatus useful for diagnosis by acquiring ultrasonic images within a subject, e.g., within a human body. FIG. 11 is a block diagram of an ultrasonic diagnostic imaging apparatus 90. The ultrasonic diagnostic imaging apparatus 90 includes a transducer 91, IC (Integrated Circuit) chips 92-94, and a monitor 95.

The transducer 91 transmits ultrasonic waves, and receives the ultrasonic waves (echo) reflected by the subject. The IC chip 92 transmits high-voltage pulses to the transducer 91, and receives voltage signals (echo signals) corresponding to echoes from the transducer 91. The IC chip 92 transmits the echo signals to the IC chip 93. The IC chip 93 receives the echo signals, and, after an amplifier amplifies the echo signals, converts the amplified echo signals into digital values. The IC chip 93 transmits the echo signals converted into the digital values to the IC chip 94. The IC chip 94 receives the echo signals converted into the digital values, generates images by executing image processing based on the echo signals converted into the digital values, and displays the images on the monitor 95.

A connection between the transducer 91 and the IC chip 92 involves using an analog cable. This analog cable is a bundle of coaxial cables of N-ch. The analog cable transfers high-voltage (e.g., equal to or higher than 100V) signals on one hand, and is high in cost for propagating weak signals from the transducer 91 with low noises on the other hand. The transducer 91 is provided within the probe, and the IC chips 92-94 and the monitor 95 are provided on an apparatus body. An ultrasonic diagnosis is conducted by applying the probe to a diagnosis region, and hence the diagnosis region has a limitation depending on a length of the cable as the case may be. A contact between the cable and the human body entails taking account of sanitation. Known therefore is a technology of providing a cableless structure between the probe and the monitor 95 by causing the probe to accommodate the transducer 91 and the IC chips 92-94, and wirelessly connecting the probe to the monitor 95.

[Patent document 1] Japanese National Publication of International Patent Application No. 2002-530142
[Patent document 2] Japanese National Publication of International Patent Application No. 2010-528696
[Patent document 3] Japanese National Publication of International Patent Application No. 2003-506172
[Patent document 4] Japanese Laid-open Patent Publication No. 2007-244580

SUMMARY

According to an aspect of the application, an ultrasonic probe includes: a transducer transmitting and receiving ultrasonic waves, and converting ultrasonic signals into voltage signals and vice versa; a first circuit configured to transmit pulse voltage signals to the transducer and receive the voltage signals from the transducer; a second circuit configured to convert the voltage signals received from the first circuit into digital values from analog values; a battery unit configured to supply electric power to the first circuit and the second circuit; and a substrate being provided with the transducer, the first circuit and the second circuit, the first circuit being disposed on a first surface of the substrate, and the second circuit being disposed on a second surface opposite to the first surface of the substrate.

DESCRIPTION OF EMBODIMENT

When providing the cableless structure between the probe and the monitor 95, it follows that the probe accommodates a power source for supplying electric power to the transducer 91 and the IC chips 92-94. Accordingly, this entails decreasing power consumption of the probe. A scheme for decreasing the power consumption is made by stepping down a pulse voltage to a great degree (e.g., the voltage is varied to 25V from 100V).

However, when the pulse voltage is stepped down, transmission/reception power of the ultrasonic waves is also attenuated, and hence such an apprehension exists that the images generated based on the echo signals might be deteriorated due to noises being mixed into the echo signals.

An ultrasonic probe according to an embodiment will hereinafter be described with reference to the drawings. A configuration of the ultrasonic probe, which will be illustrated below, is an exemplification, and the configuration of the ultrasonic probe according to the embodiment is not limited to the configuration that will hereinafter be illustrated.

Figure 1:
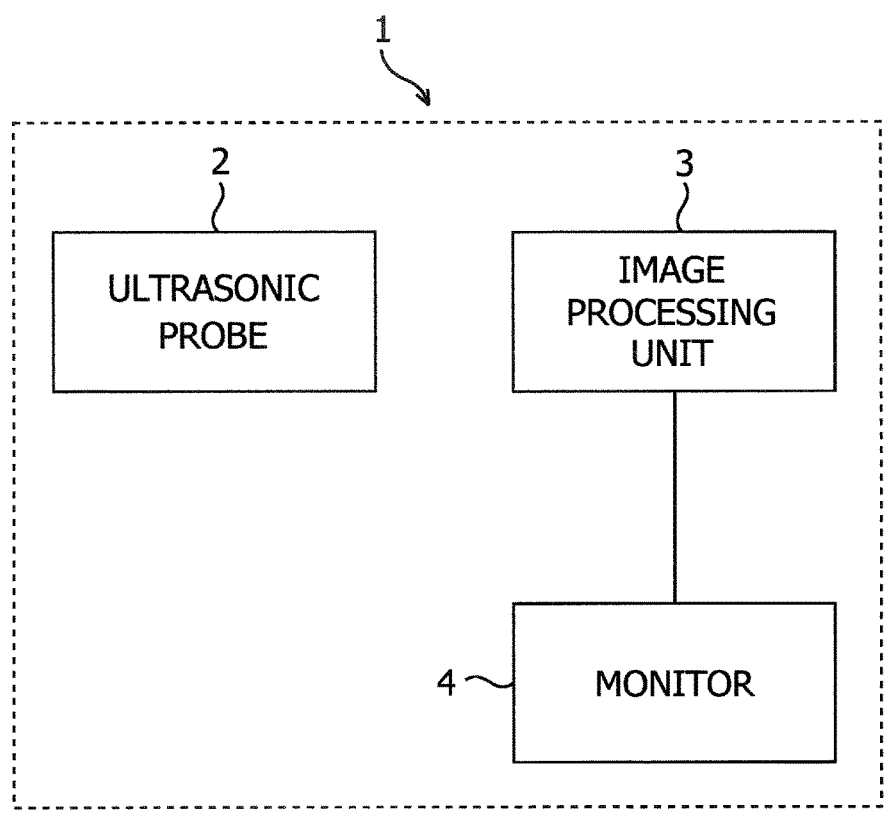
FIG. 1 is a block diagram illustrating one example of a configuration of an ultrasonic diagnostic imaging apparatus.

FIG. 1 is a block diagram illustrating one example of a configuration of an ultrasonic diagnostic imaging apparatus 1. The ultrasonic diagnostic imaging apparatus 1 includes an ultrasonic probe 2, an image processing unit 3 and a monitor 4. The ultrasonic probe 2 and the image processing unit 3 are wirelessly mutually communicable. In other words, a cableless connection is established between the ultrasonic probe 2 and the image processing unit 3. A wired connection is established via a cable between the image processing unit 3 and the monitor 4. However, a wireless connection may also be applied to between the image processing unit 3 and the monitor 4.

Figure 2:
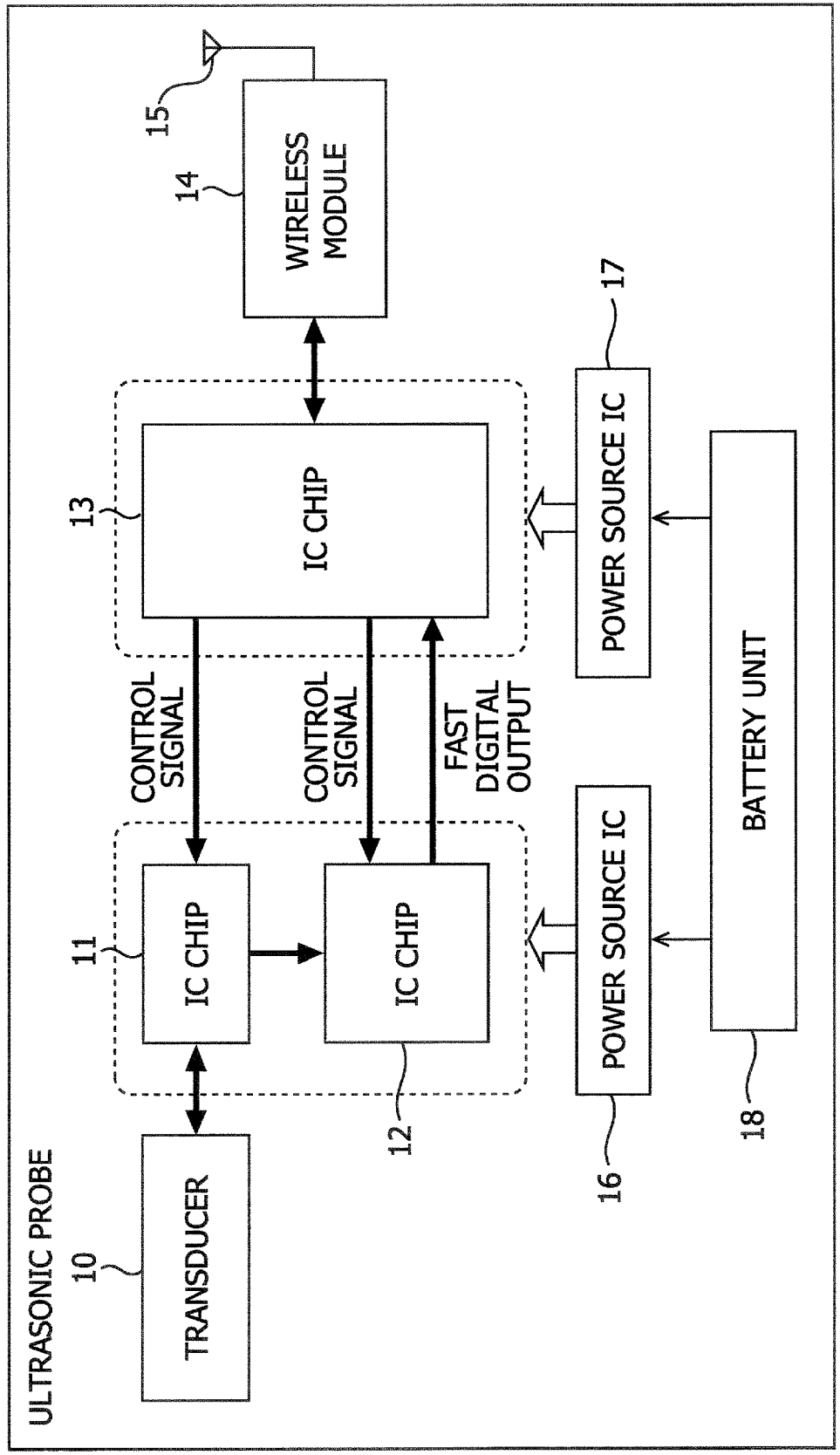
FIG. 2 is a block diagram illustrating one example of a configuration of an ultrasonic probe.

FIG. 2 is a block diagram illustrating one example of a configuration of the ultrasonic probe 2. The ultrasonic probe 2 includes a transducer 10, an IC chip (first IC) 11, an IC chip (second IC) 12, an IC chip (third IC) 13, a wireless module 14, an antenna 15, power source ICs 16, 17, and a battery unit 18. The ultrasonic probe 2 accommodates the transducer 10, the IC chips 11-13, the wireless module 14, the antenna 15, the power source ICs 16, 17, and the battery unit 18. The IC chip 11 is one example of a first circuit. The IC chip 12 is one example of a second circuit. The IC chip 13 is one example of a third circuit.

The transducer 10 transmits ultrasonic waves and receives the ultrasonic waves (echo) reflected from a subject. The transducer 10 converts ultrasonic signals into voltage signals, and vice versa. The transducer 10 has a plurality of oscillators arrayed in a rectangular shape. The oscillator has a piezoelectric substance instanced by a piezoelectric element, and electrodes formed on both sides of the piezoelectric substance. The piezoelectric substances are stretched and contracted by applying voltages to the electrodes, whereby the ultrasonic waves are generated from the respective oscillators. Each oscillator receives the ultrasonic waves, and is thereby stretched and contracted to generate electric signals. The transducer 10 transmits, based on the electric signals generated by each oscillator, voltage signals corresponding to echoes (which will hereinafter be termed echo signals) to the IC chip 11.

Figure 3:
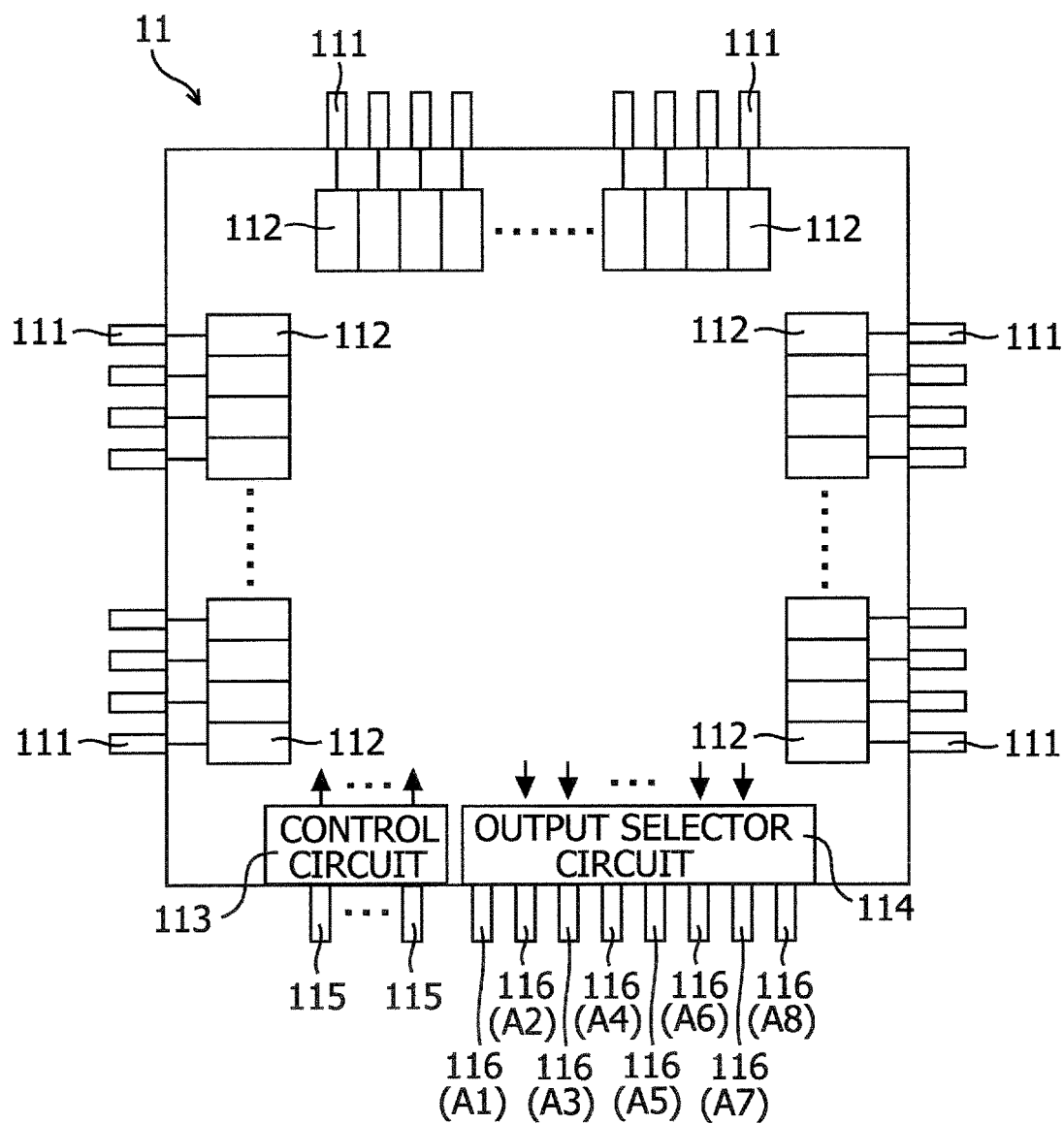
FIG. 3 is a diagram illustrating one example of a configuration of an IC chip (first IC).

The IC chip 11 transmits high-voltage pulses (pulse voltage signals) to the transducer 10, and receives the echo signals from the transducer 10. The IC chip 11 transmits the echo signals to the IC chip 12. FIG. 3 is a diagram illustrating one example of a configuration of the IC chip 11. The IC chip 11 includes a plurality of connection terminals 111 and a plurality of transmission/reception circuit 112. The connection terminals 111 are used for a connection to the transducer 10. The transmission/reception circuit 112 transmits the pulse voltage signals to the transducer 10 via the connection terminals 111, and receives the echo signals from the transducer 10 via the connection terminals 111. The plurality of connection terminals 111 is arranged along one side or a plurality of sides of the IC chip 11. In an example illustrated in FIG. 3, the plurality of connection terminals 111 is arranged around the IC chip 11 along three sides of the IC chip 11.

The IC chip 11 further includes a control circuit 113, an output selector circuit 114, a plurality of control terminals 115, and a plurality of output terminals 116. The control circuit 113 receives a control signal from the IC chip 13 via the control terminal 115, and controls, based on the control signal, an operation of the IC chip 11. An arbitrary channel (a transmission path including the connection terminals 111 and the transmission/reception circuit 112) is selected based on the control signal to be inputted to the control circuit 113, and the IC chip 11 transmits the pulse voltage signals to the transducer 10.

The output selector circuit 114 selects, based on the control signal to be inputted to the control circuit 113, the echo signals to be inputted to the output selector circuit 114, and outputs the selected echo signals to the IC chip 12 via the plurality of output terminals 116. Accordingly, the arbitrary channel (the transmission path including the connection terminals 111 and the transmission/reception circuit 112) is selected based on the control signal to be inputted to the control circuit 113, and the IC chip 11 transmits the echo signals to the IC chip 12. The output terminals 116 are used for a connection between the IC chip 11 and the IC chip 12. In the example illustrated in FIG. 3, the plurality of output terminals 116 is arranged at the IC chip 11 along one side of the IC chip 11. The output terminals 116 are arranged along the side different from the sides along which to arrange the connection terminals 111 of the IC chip 11. In the example illustrated in FIG. 3, the echo signals for eight channels at maximum are transmitted to the IC chip 12 via the plurality of output terminals 116 (A1-A8).

Figure 4:
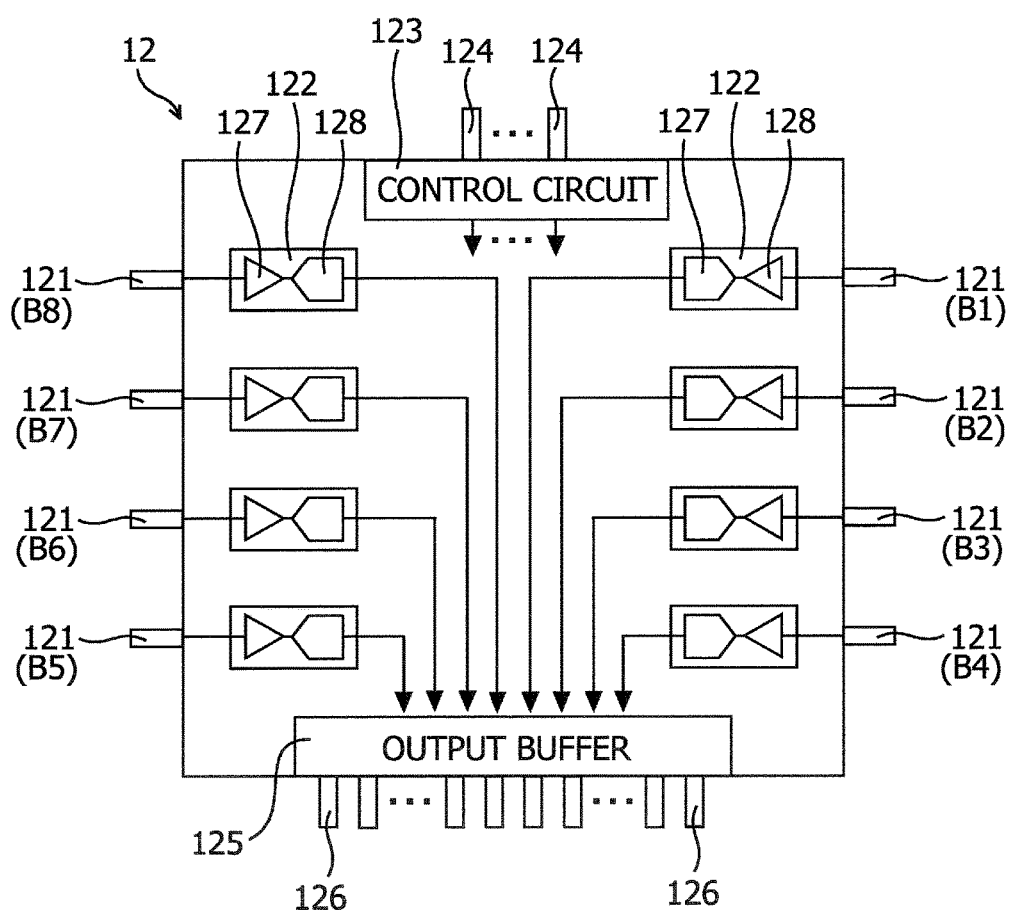
FIG. 4 is a diagram illustrating one example of a configuration of an IC chip (second IC).

The IC chip 12, which receives the echo signals from the IC chip 11, amplifies the received echo signals by an amplifier, and converts the amplified echo signals into digital values from analog values. FIG. 4 is a diagram illustrating one example of a configuration of the IC chip 12. The IC chip 12 includes a plurality of connection terminals 121, a plurality of signal adjusting circuits 122, a control circuit 123, a plurality of control terminals 124, an output buffer 125, and a plurality of output terminals 126. The plurality of connection terminals 121 is used for a connection between the IC chip 11 and the IC chip 12. The plurality of output terminals 126 is employed for a connection between the IC chip 12 and the IC chip 13. The IC chip 12 receives the echo signals from the IC chip 11, and may convert the received echo signals into the digital values from the analog values. In other words, the IC chip 12 may convert the echo signals into the digital values from the analog values without amplifying the echo signals.

The signal adjusting circuits 122 is instanced by an AFE (Analog Front End). The signal adjusting circuits 122 includes an amplifier 127 and an ADC (Analog to Digital Converter) 128. The amplifier 127 amplifies the echo signals to be inputted. The ADC 128 converts the echo signals to be inputted into the digital values from the analog values, and outputs the digital echo signals. In other words, the ADC 128 converts the analog echo signals into the digital echo signals. The echo signals outputted from the ADC 128 are transmitted to the IC chip 13 via the output buffer 125 and the output terminals 126. The IC chip 12 converts the echo signals into the digital values from the analog values without amplifying the echo signals, in which case the amplifier 127 may be omitted.

The control circuit 123 receives the control signal from the IC chip 13 via the control terminal 124, and controls, based on the control signal, the operation of the IC chip 12. The control signal inputted via the control terminal 124 contains a signal for controlling a gain of the amplifier 127.

In an example illustrated in FIG. 4, the signal adjusting circuits 122 are arranged for the respective channels, in which the echo signals for the eight channels at the maximum are amplified and A/D-converted. In the example illustrated in FIG. 4, the four connection terminals 121 are arranged along each of the two sides, taking a face-to-face relationship with each other, of the IC chip 12. Therefore, the echo signals for the four channels are inputted to each of the two face-to-face sides of the IC chip 12. In the example illustrated in FIG. 4, the control terminals 124 are arranged along one side different from the sides along which to arrange the connection terminals of the IC chip 12, while the output terminals 126 are arranged along the side taking the face-to-face relationship with the side along which to arrange the control terminals 124 of the IC chip 12. The IC chip 12 is therefore configured to separate portions to which the analog echo signals are inputted from portions from which the digital echo signals are outputted. The IC chip 12 is also configured to separate portions to which the analog echo signals are inputted from portions to which the control signals are inputted.

The IC chip 13 transmits the control signals to the IC chips 11, 12. The IC chip 13 receives the digital echo signals from the IC chip 12. The IC chip 13 generates image signals by executing image processing based on the echo signals. The IC chip 13 transmits the image signals to the wireless module 14. The wireless module 14 receives the image signals from the IC chip 13. The wireless module 14 wirelessly transmits the image signals to a wireless module possessed by the image processing unit 3 via the antenna 15. The image processing unit 3 displays images on the monitor 4, based on the image signals. The image processing unit 3 is a computer including a processor instanced by a CPU (Central Processing Unit), and memories (storage units) instanced by a ROM (Read Only Memory) and a RAM (Random Access Memory). The monitor 4 is a display device instanced by a CRT (Cathode Ray Tube), a liquid crystal display, a plasma display and an organic EL (electroluminescence) display.

The IC chip 13 may transmit the echo signals to the wireless module 14, and the wireless module 14 may receive the echo signals from the IC chip 13. In this case, the wireless module 14 wirelessly transmits the echo signals to the wireless module possessed by the image processing unit 3 via the antenna 15. The image processing unit 3 generates the image signals by executing the image processing based on the echo signals, and displays the images on the monitor 4 on the basis of the image signals.

A connection wire (signal line) for connecting the transducer 10 to the IC chip 11 and a connection wire (signal line) for connecting the IC chip 11 to the IC chip 12, are wires via which to transmit and receive the weak echo signals. The connection wire for connecting the transducer 10 to the IC chip 11 and the connection wire for connecting the IC chip 11 to the IC chip 12, therefore entail taking sufficient countermeasures against noises. Described are the countermeasures against the noises caused in the connection wire for connecting the transducer 10 to the IC chip 11 and the connection wire for connecting the IC chip 11 to the IC chip 12. The connection wire for connecting the transducer 10 to the IC chip 11 is one example of a first connection wire. The connection wire for connecting the IC chip 11 to the IC chip 12 is one example of a second connection wire.

The countermeasures against the noises are exemplified by avoiding crossing, as may become a noise source, between the signal wires on a substrate equipped in the ultrasonic probe 2, and shielding the signal wires. The noise source is instanced by switching noises and radiant noises from outside.

Figure 5A:
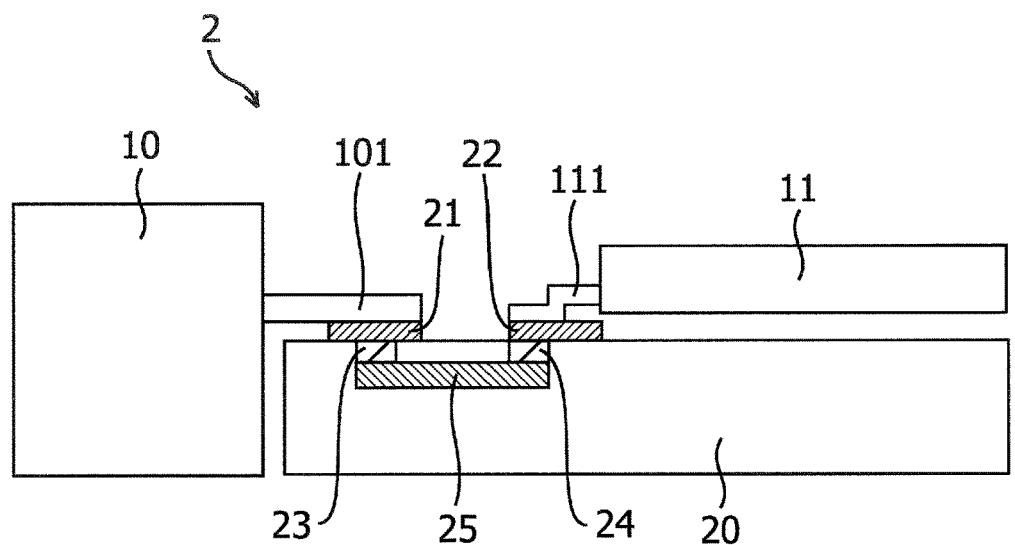
FIG. 5A is a partial sectional view of the ultrasonic probe.
Figure 5B:
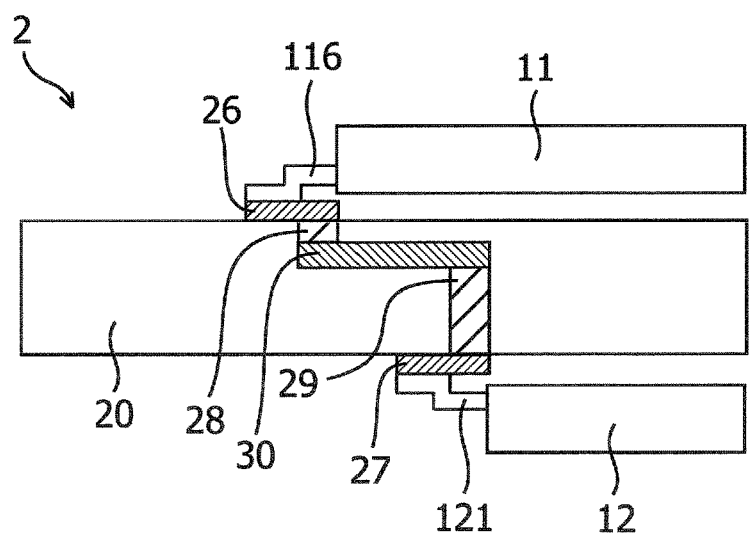
FIG. 5B is a partial sectional view of the ultrasonic probe.
Figure 5C:
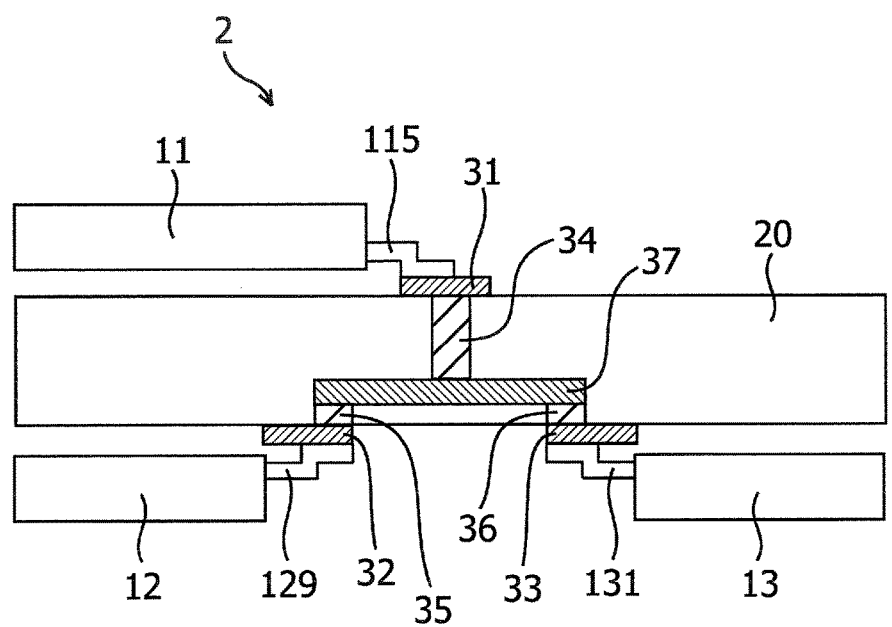
FIG. 5C is a partial sectional view of the ultrasonic probe.

FIGS. 5A-5C are partial sectional views of the ultrasonic probe 2. As illustrated in FIGS. 5A-5C, a circuit board 20 is provided with the transducer 10 and the IC chips 11-13, which are connected together by using inner layer wires and through-holes of the circuit board (substrate) 20. The inner layer wire is, e.g., a metal wire composed of copper (Cu) and other equivalent metals. The through-hole includes a hole formed in the circuit board 20 and copper plating applied over a side wall of the hole. The through-hole is also called a via. The transducer 10 is fitted to a side surface of the circuit board 20. The circuit board 20 is, e.g., a PCB (Printed Circuit Board). The circuit board 20 is one example of a substrate. The circuit board 20 is configured to have 2 or more layered wiring structure, i.e., a multi-layered wiring structure, thereby enabling a restraint of occurrence of crosstalks on upper-and-lower/right-and-left layers in an interior of the circuit board 20. A periphery of the inner layer wire of the circuit board 20 is ground-shielded, thereby enabling a restraint of mixing of the noises from an outside of the ultrasonic probe 2.

FIG. 5A depicts the connection wire for connecting the transducer 10 to the IC chip 11. The IC chip 11 is disposed on an upper surface (first surface) of the circuit board 20. A connector 21 and a pad (electrode) 22 are formed on the upper surface of the circuit board 20. Through-holes 23, 24 and an inner layer wire 25 are formed in the interior of the circuit board 20. The connector 21 is electrically connected to the through-hole 23, and the pad 22 is electrically connected to the through-hole 24. The inner layer wire 25 is electrically connected to each of the through-holes 23, 24. The connection terminal 111 of the IC chip 11 is electrically connected to the pad 22.

A connection terminal 101 of the transducer 10 contacts the connector 21 and is thus electrically connected to the connector 21, thereby establishing the connection between the transducer 10 and the IC chip 11. A ground wire connected to the ground is formed along peripheries of the through-holes 23, 24 and the inner layer wire 25, whereby the peripheries of the through-holes 23, 24 and the inner layer wire 25 are ground-shielded. Thus restrained is the mixing of the noises into the echo signals propagating (passing) through the connection wire (inclusive of the through-holes 23, 24 and the inner layer wire 25 in the example depicted in FIG. 5A) for connecting the transducer 10 to the IC chip 11.

FIG. 5B illustrates a connection wire for connecting the IC chip 11 to the IC chip 12. The IC chip 11 is disposed on the upper surface of the circuit board 20, while the IC chip 12 is disposed on a lower surface (second surface) of the circuit board 20. The lower surface of the circuit board 20 is a surface on an opposite side to the upper surface of the circuit board 20. A pad (electrode) 26 is formed on the upper surface of the circuit board 20. A pad (electrode) 27 is formed on the lower surface of the circuit board 20. Through-holes 28, 29 and an inner layer wire 30 are formed in the interior of the circuit board 20.

The pad 26 is electrically connected to the through-hole 28, and the pad 27 is electrically connected to the through-hole 29. The inner layer wire 30 is electrically connected to each of the through-holes 28, 29. The output terminal 116 of the IC chip 11 is electrically connected to the pad 26. The connection terminal 121 of the IC chip 12 is electrically connected to the pad 27. The IC chip 11 is electrically connected to the IC chip 12 through these electrical connections.

As illustrated in FIG. 5B, the IC chip 11 is disposed on the upper surface of the circuit board 20, while the IC chip 12 is disposed on the lower surface of the circuit board 20. In other words, the IC chip 11 and the IC chip 12 are disposed on the upper and lower surfaces (back and front surfaces) of the circuit board 20. It is therefore feasible to shorten the connection wire (inclusive of the through-holes 28, 29 and the inner layer wire 30 in the example depicted in FIG. 5B) for connecting the IC chip 11 to the IC chip 12. The connection wire for connecting the IC chip 11 to the IC chip 12 may be made shorter than disposing both of the IC chips 11, 12 on the same surface of the circuit board 20. The connection wire for connecting the IC chip 11 to the IC chip 12 is shortened, thereby restraining the mixing of the noises into the echo signals propagating through the connection wire for connecting the IC chip 11 to the IC chip 12. An area of the connection wire for connecting the IC chip 11 to the IC chip 12 may be made smaller than disposing both of the IC chips 11, 12 on the same surface of the circuit board 20.

The ground wire connected to the ground is formed along peripheries of the through-holes 28, 29 and the inner layer wire 30, whereby the peripheries of the through-holes 28, 29 and the inner layer wire 30 are ground-shielded. Thus restrained is the mixing of the noises into the echo signals propagating through the connection wire for connecting the IC chip 11 to the IC chip 12.

FIG. 5C illustrates the connection wire for connecting the IC chip 11 to the IC chip 13 and the connection wire for connecting the IC chip 12 to the IC chip 13. The IC chip 11 is disposed on the upper surface of the circuit board 20, while the IC chips 12, 13 are disposed on the lower surface of the circuit board 20. In the example illustrated in FIG. 5C, the IC chip 13 is disposed on the lower surface of the circuit board 20 and may also be disposed on the upper surface of the circuit board 20. A pad (electrode) 31 is formed on the upper surface of the circuit board 20. Pads (electrodes) 32, 33 are formed on the lower surface of the circuit board 20. Through-holes 34, 35, 36 and an inner layer wire 37 are formed in the interior of the circuit board 20.

The pad 31 is electrically connected to the through-hole 34; the pad 32 is electrically connected to the through-hole 35; and the pad 33 is electrically connected to the through-hole 36. The inner layer wire 37 is electrically connected to each of the through-holes 34, 35, 36. The control terminal 115 of the IC chip 11 is electrically connected to the pad 31. The IC chip 12 includes a plurality of outer terminals 129. The outer terminal 129 is the control terminal 124 or the output terminal 126. The outer terminal 129 of the IC chip 12 is electrically connected to the pad 32. The IC chip 13 has a plurality of outer terminals 131. The outer terminal 131 is the control terminal or the signal terminal. The outer terminal 131 of the IC chip 13 is electrically connected to the pad 33. The IC chip 11 is electrically connected to the IC chip 13, and the IC chip 12 is electrically connected to the IC chip 13. Through these electrical connections, the IC chip 11 is electrically connected to the IC chip 13, and the IC chip 12 is electrically connected to the IC chip 13.

The ground wire connected to the ground is formed along peripheries of the through-holes 34, 35, 36 and an inner layer wire 37, whereby the peripheries of the through-holes 34, 35, 36 and the inner layer wire 37 are ground-shielded. Thus restrained is the mixing of the noises into the control signals propagating through the connection wire (inclusive of the through-holes 34, 36 and the inner layer wire 37 in the example depicted in FIG. 5C) for connecting the IC chip 11 to the IC chip 13. Restrained also is the mixing of the noises into the control signals or the echo signals propagating through the connection wire (inclusive of the through-holes 34, 35 and the inner layer wire 37 in the example depicted in FIG. 5C) for connecting the IC chip 12 to the IC chip 13.

Figure 6:
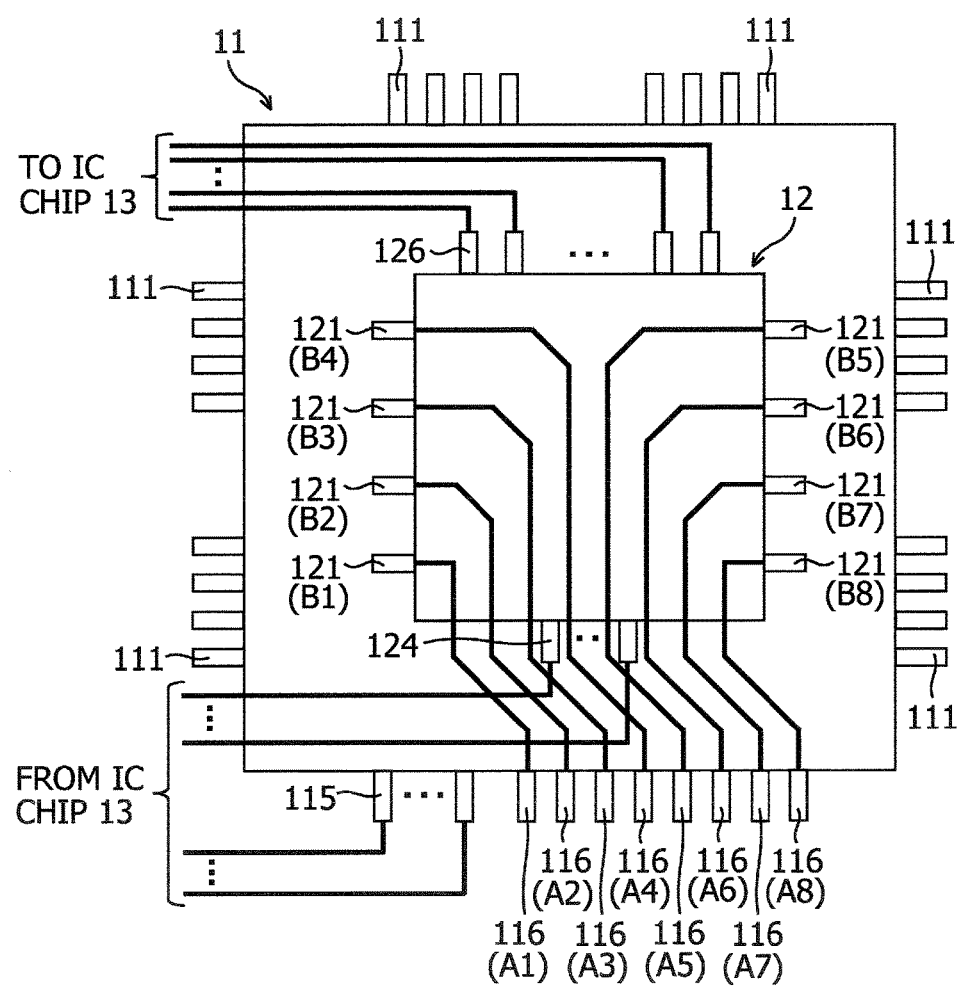
FIG. 6 is a diagram illustrating one example of how the IC chips (first IC, second IC) are disposed.

FIG. 6 is a diagram illustrating one example of how the IC chips 11, 12 are disposed. FIG. 6 perspectively illustrates, as viewed on plane, a position of disposing the IC chip 11 on the circuit board 20 and a position of disposing the IC chip 12 on the circuit board 20. FIG. 6 depicts a plurality of wires for connecting the output terminals 116 of the IC chip 11 to the connection terminals 121 of the IC chip 12. The wires for connecting the output terminals 116 of the IC chip 11 to the connection terminals 121 of the IC chip 12 are the connection wires for connecting the IC chip 11 to the IC chip 12. Each of the plurality of connection wires for connecting the IC chip 11 to the IC chip 12 is formed within the circuit board 20 so as not to intersect each other as viewed on the plane. Occurrence of the crosstalks in the plurality of connection wires for connecting the IC chip 11 to the IC chip 12 is thereby restrained. The connection terminals 111 of the IC chip 11 are formed to surround the connection terminals 121 of the IC chip 12 as viewed on the plane. The occurrence of the crosstalks at the connection terminals is restrained by not causing the intersections between the connection terminals of the IC chip 11 and the connection terminals of the IC chip 12.

As illustrated in FIG. 6, the wires are formed within the circuit board 20 so that the plurality of connection wires for connecting the IC chip 11 to the IC chip 12 does not intersect the plurality of wires connected to the output terminals 126 of the IC chip 12 as viewed on the plane. The wires connected to the output terminals 126 of the IC chip 12 are the connection wires for connecting the IC chip 12 to the IC chip 13, and are also the wires through which the digital signals transmitted to the IC chip 13 from the IC chip 12 propagate. The connection wires for connecting the IC chip 12 to the IC chip 13 are one example of second connection wires.

The echo signals transmitted to the IC chip 12 from the IC chip 11 propagate through the connection wires for connecting the IC chip 11 to the IC chip 12. The echo signals transmitted to the IC chip 13 from the IC chip 12 propagate through the connection wires connected to the output terminals 126 of the IC chip 12. The echo signals transmitted to the IC chip 12 from the IC chip 11 are weak analog signals. On the other hand, the echo signals transmitted to the IC chip 13 from the IC chip 12 are fast digital signals that entail taking account of being affected by switching noises. Therefore, the connection wires are formed within the circuit board 20 so that the connection wires through which the echo signals transmitted to the IC chip 12 from the IC chip 11 propagate do not intersect the connection wires through which the echo signals transmitted to the IC chip 13 from the IC chip 12 propagate as viewed on the plane. The mixing of the noises into the echo signals transmitted to the IC chip 12 from the IC chip 11 is thereby restrained. It is therefore feasible to take the countermeasures against the noises with respect to the wires each exhibiting a high sensitivity to the noise.

The connection wires for connecting the IC chip 11 to the IC chip 12 and the wires connected to the control terminals 124 of the IC chip 12 are arranged on different layers of the circuit board 20. Consequently, as depicted in FIG. 6, the connection wires for connecting the IC chip 11 to the IC chip 12 partially intersect the wires connected to the control terminals 124 of the IC chip 12 as viewed on the plane. The control signals transmitted to the IC chip 12 from the IC chip 13 propagate through the wires connected to the control terminals 124 of the IC chip 12. The control signals transmitted to the IC chip 12 from the IC chip 13 are low-speed digital signals, and are therefore small in degree of being affected by the mixing of the noises into the echo signals transmitted to the IC chip 12 from the IC chip 11.

Referring back to FIG. 2, the power source ICs 16, 17 and the battery unit 18 will be described. The power source IC 16 controls the power supplied to the IC chips 11, 12. To be specific, the power source IC 16 steps up or down a voltage of the power inputted from the battery unit 18, and thus supplies the power to the IC chips 11, 12. The power source IC 17 controls the power supplied to the IC chip 13. To be specific, the power source IC 17 steps up or down the voltage of the power inputted from the battery unit 18, and thus supplies the power to the IC chips 13. The battery unit 18, which is connected to an outside power source, is supplied with the power from the outside power source, and accumulates the power. The battery unit 18 supplies the power to the IC chips 11, 12 via the power source IC 16, and also supplies the power the IC chip 13 via the power source IC 17.

As illustrated in FIG. 2, the IC chips 11, 12 are supplied with the power from the battery unit 18 via the power source IC 16, and the IC chip 13 is supplied with the power from the battery unit 18 via the power source IC 17. The IC chips 11, 12 receive the inputting of the analog echo signals, and are therefore supplied with the power from the battery unit 18 via the power source IC 16. While on the other hand, the IC chip 13 receives the inputting of the digital echo signals, and is therefore supplied with the power from the battery unit 18 via the power source IC 17 different from the power source IC 16. The IC chips 11, 12 are actuated by the same power source IC (which is the power source IC 16 in FIG. 2), while the IC chip 13 is actuated by another power source IC (which is the power source IC 17 in FIG. 2). The power source noises of the IC chip 13 are thereby enabled to be restrained from being transferred to the IC chips 11, 12 via the power source IC. Accordingly, the noises are restrained from being mixed into the echo signals inputted to the IC chips 11, 12.

The power source ICs 16, 17 are, e.g., a DC-DC converter or an LDO (Low Drop Out). The DC-DC converter is also called a switching regulator, and the LDO is also called a linear regulator or a series regulator. The DC-DC converter converts the power (conversion of the voltage and an electric current) by fast switching that uses a semiconductor device, and hence causes occurrence of switching noises. Each of the oscillators of the transducer 10 resonates at a natural frequency (e.g., 6.5 MHz).

The power source IC 16 is the DC-DC converter, in which case an operation frequency (switching frequency) of the switching operation of the power source IC 16 is deviated from a resonance frequency of each oscillator of the transducer 10. For example, a predetermined frequency band (a width of the predetermined frequency) including the resonance frequency of each oscillator of the transducer 10 is different from the operation frequency of the switching operation of the power source IC 16. This enables the restraint of the mixing of the noises into the echo signals transmitted to the IC chip 11 from the transducer 10 and the echo signals transmitted to the IC chip 12 from the IC chip 11. For instance, the predetermined frequency band including the resonance frequency of each oscillator of the transducer 10 may be set equal to or higher than 6.5 MHz but equal to or lower than 9.5 MHz, and the operation frequency of the switching operation of the power source IC 16 may also be set at 10 MHz. Note that when the power source IC 17 is the DC-DC converter, the operation frequency of the switching operation of the power source IC 17 may be deviated from the resonance frequency of each oscillator of the transducer 10.

Figure 7:
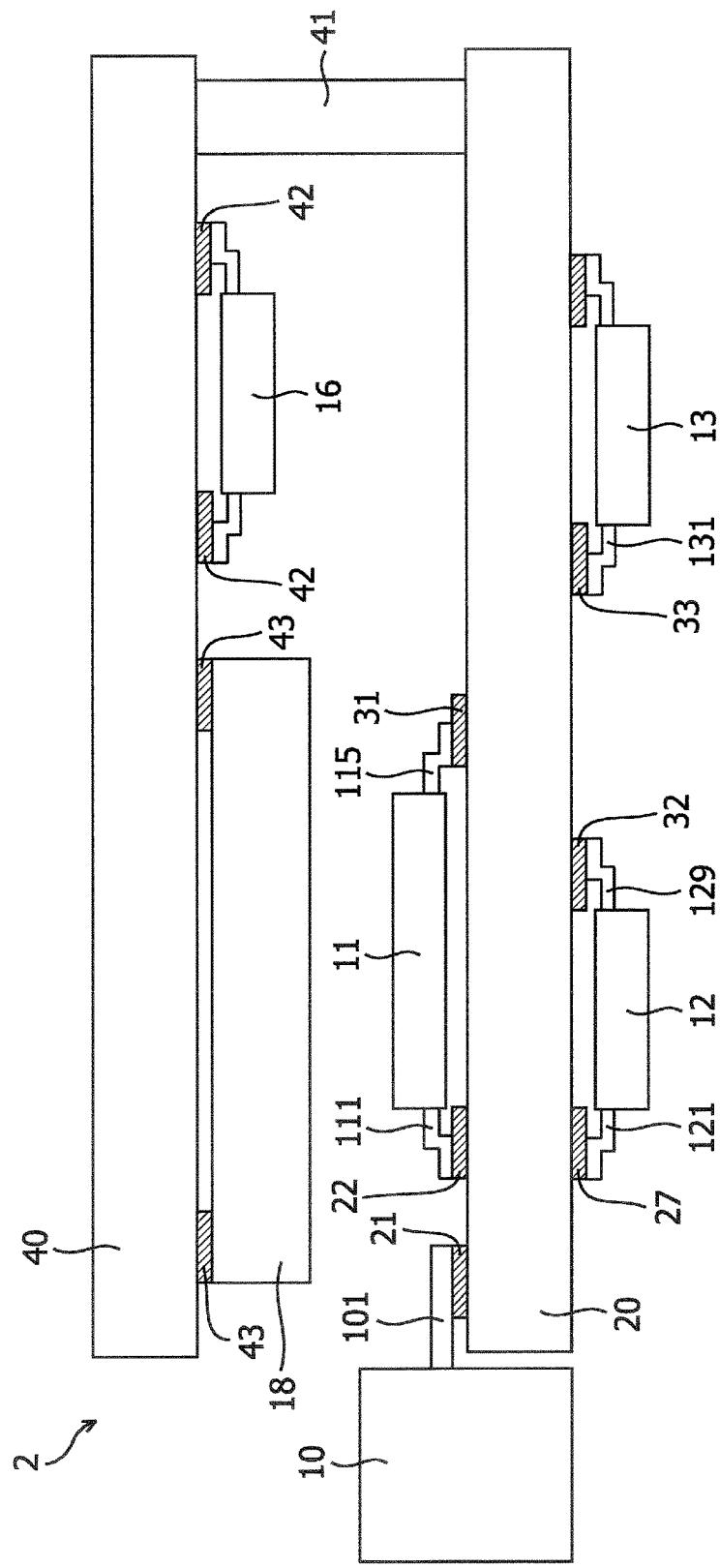
FIG. 7 is a diagram illustrating one example of how a battery unit is disposed.

FIG. 7 is a diagram illustrating one example of how the battery unit 18 is disposed. As illustrated in FIG. 7, the ultrasonic probe 2 includes the circuit board 20, a circuit board (substrate) 40 disposed in the face-to-face relationship with the circuit board 20, and a connector 41 disposed between the circuit board 20 and the circuit board 40. The circuit board 40 is one example of a second substrate. The circuit board 40 is provided with the power source ICs 16, 17 and the battery unit 18. A support rod (unillustrated) is provided on the upper surface (main surface) of the circuit board 20, and the circuit board 40 is fixed to the support rod of the circuit board 20. The power source ICs 16, 17 and the battery unit 18 are disposed on the upper surface of the circuit board 40. Note that an illustration of the power source IC 17 is omitted in FIG. 7. The upper surface of the circuit board 40 is a surface on the side opposite to the upper surface of the circuit board 20. Pads (electrodes) 42, 43 are formed on the upper surface of the circuit board 40.

The power source ICs 16, 17 are electrically connected to the pad 42, the battery unit 18 is electrically connected to the pad 43. The power source ICs 16, 17 and the battery unit 18 are connected to the circuit board 20 via the connector 41. To be specific, the IC chips 11, 12 are supplied with the power from the battery unit 18 via the power source IC 16 and the connector 41, and the IC chip 13 is supplied with the power from the battery unit 18 via the power source IC 17 and the connector 41.

As illustrated in FIG. 7, the battery unit 18 is disposed in the face-to-face relationship with the IC chip 11, and a space is provided between the IC chip 11 and the battery unit 18. In other words, in the ultrasonic probe 2 depicted in FIG. 7, the IC chip 11 and the battery unit 18 are three-dimensionally packaged so that the IC chip 11 is in the face-to-face relationship with the battery unit 18. The battery unit 18 has features of being small in noise and hard to become a noise source. Therefore, the battery unit 18 is disposed in the face-to-face relationship with the IC chip 11 and thereby functions as a shield, and it is feasible to reduce the radiant noises from outside of the ultrasonic probe 2 with respect to the IC chip 11.

Figure 8:
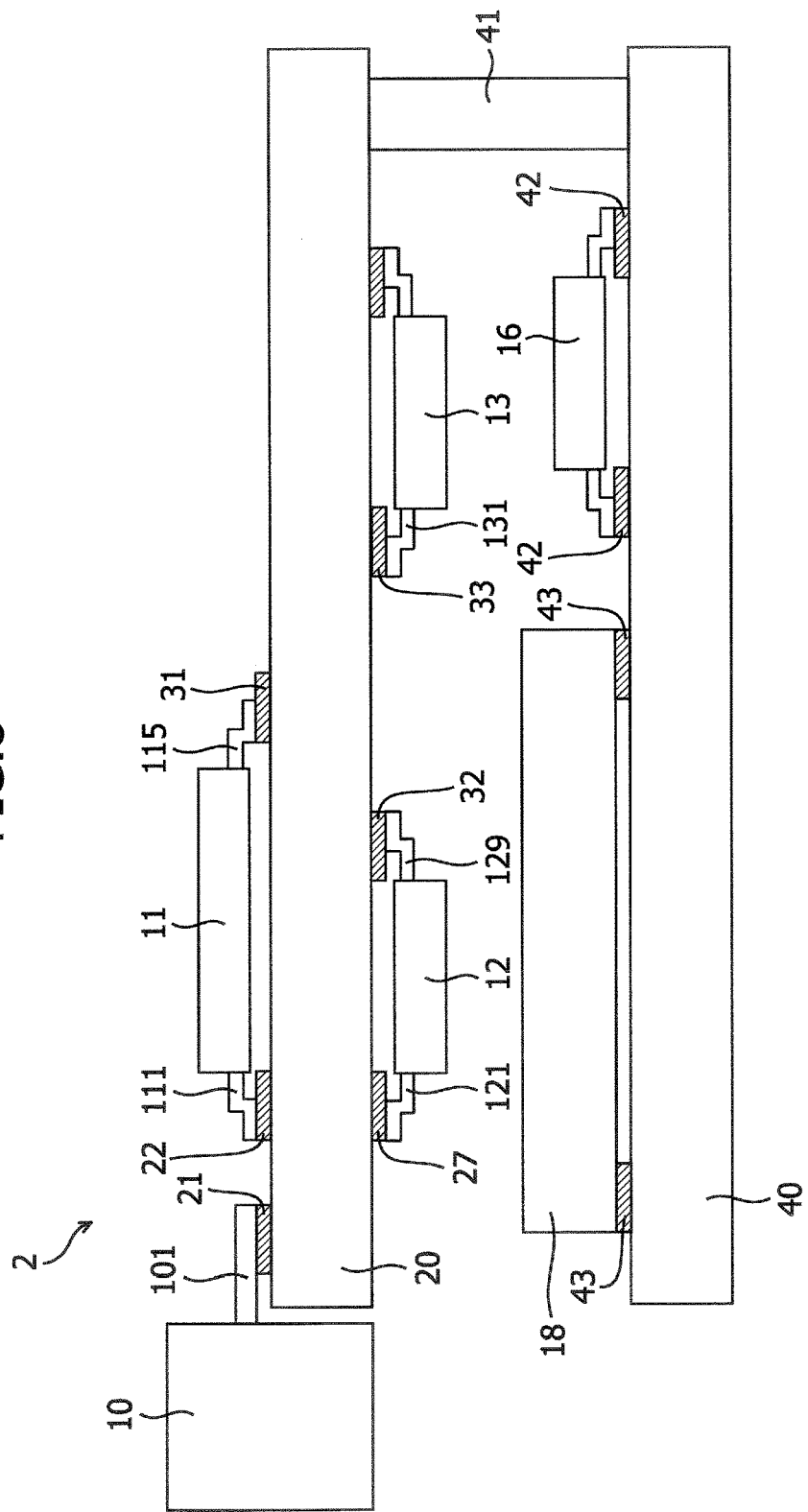
FIG. 8 is a diagram illustrating one example of how the battery unit is disposed.

The battery unit 18 may also be, as illustrated in FIG. 8, disposed in the face-to-face relationship with the IC chip 12 without being limited to the example of disposing the battery unit 18 as illustrated in FIG. 7. FIG. 8 is a diagram illustrating one example of how the battery unit 18 is disposed. A support rod (unillustrated) is provided on the lower surface of the circuit board 20, and the circuit board 40 is fixed to the support rod of the circuit board 20. The power source ICs 16, 17 and the battery unit 18 are disposed on the upper surface (main surface) of the circuit board 40. Note that the illustration of the power source IC 17 is omitted in FIG. 8. The upper surface of the circuit board 40 is a surface on the side opposite to the lower surface of the circuit board 20.

As illustrated in FIG. 8, the battery unit 18 is disposed in the face-to-face relationship with the IC chip 12, and a space is provided between the IC chip 12 and the battery unit 18. In other words, in the ultrasonic probe 2 depicted in FIG. 8, the IC chip 12 and the battery unit 18 are three-dimensionally packaged so that the IC chip 12 is in the face-to-face relationship with the battery unit 18. The battery unit 18 is disposed in the face-to-face relationship with the IC chip 12 and thereby functions as the shield, and it is feasible to reduce the radiant noises from outside of the ultrasonic probe 2 with respect to the IC chip 12.

The transducer 10 transmits and receives the ultrasonic waves, and the echo signals are transmitted to the IC chip 11 from the transducer 10 and to the IC chip 12 from the IC chip 11, during which the battery unit 18 stops being charged with electricity. During the charging of the battery unit 18 with the electricity, an IC for charging (unillustrated) operates, and hence there is such a possibility that the echo signals are affected by the switching noises due to the IC for charging. Accordingly, the battery unit 18 stops being charged with the electricity during such a period, thereby enabling inhibition of the mixing of the switching noises caused by the IC for charging into the echo signals.

Figure 9:
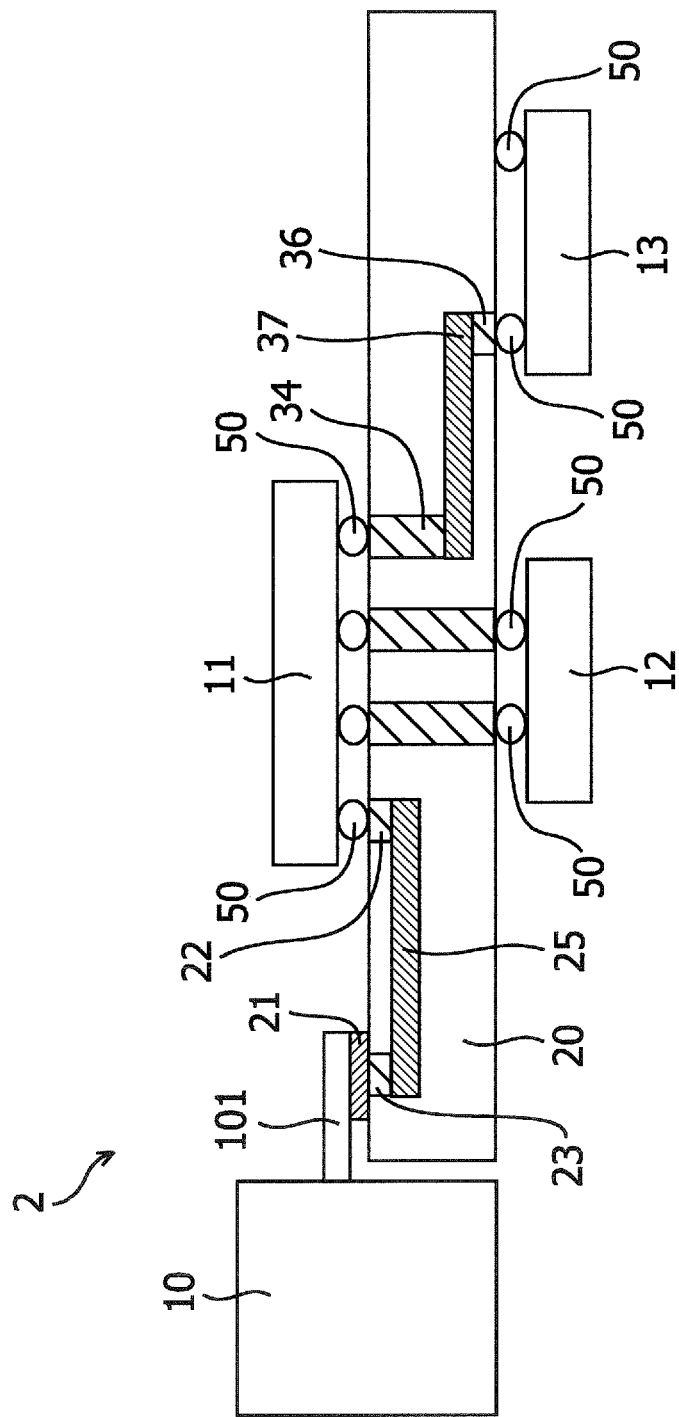
FIG. 9 is a partial sectional view of the ultrasonic probe.

Illustrated above is the example of establishing the mutual electrical connections among the IC chips 11-13 by using the terminals of the IC chips 11-13. The mutual electrical connections among the IC chips 11-13 may also be, as illustrated in FIG. 9, established by employing solder balls of BGA (Ball Grid Array) without being limited to this example. FIG. 9 is a partial sectional view of the ultrasonic probe 2. As illustrated in FIG. 9, solder balls 50 are provided between the IC chips 11-13 and the circuit board 20, thus establishing the mutual electrical connections among the IC chips 11-13.

Figure 10:
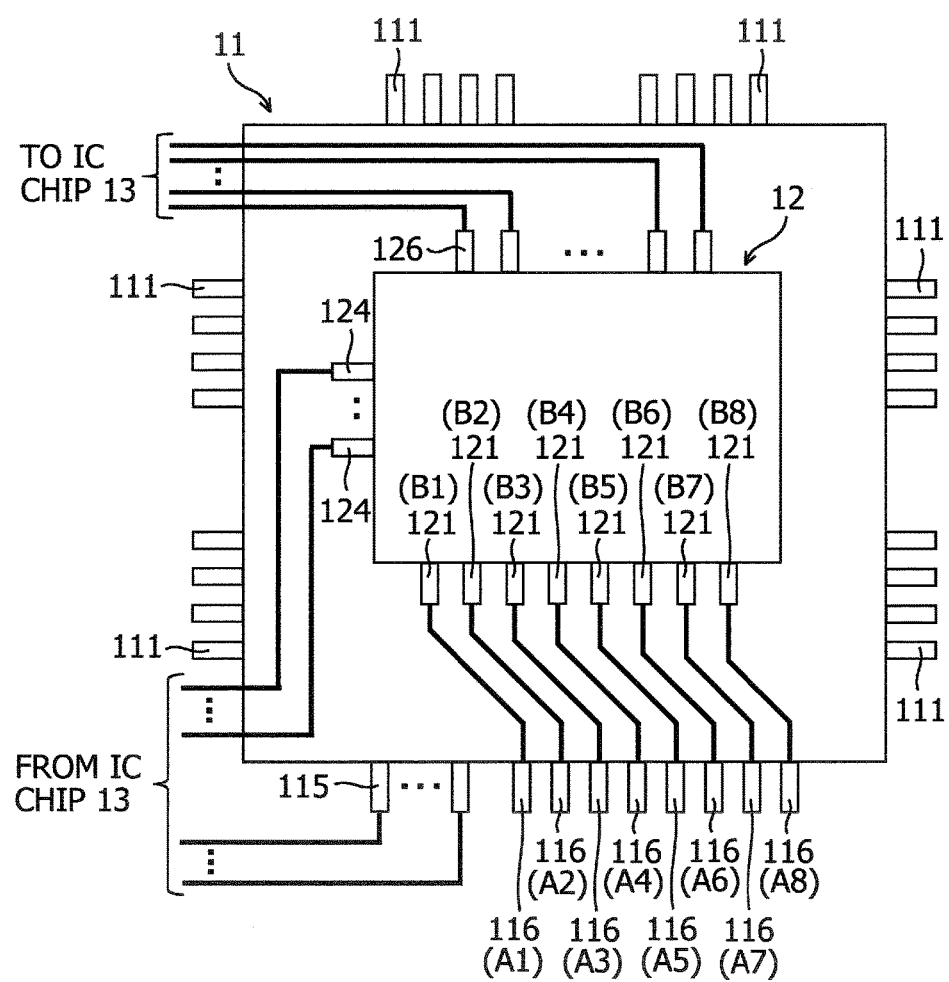
FIG. 10 is a diagram illustrating one example of how the IC chips (first IC, second IC) are disposed.
Figure 11:
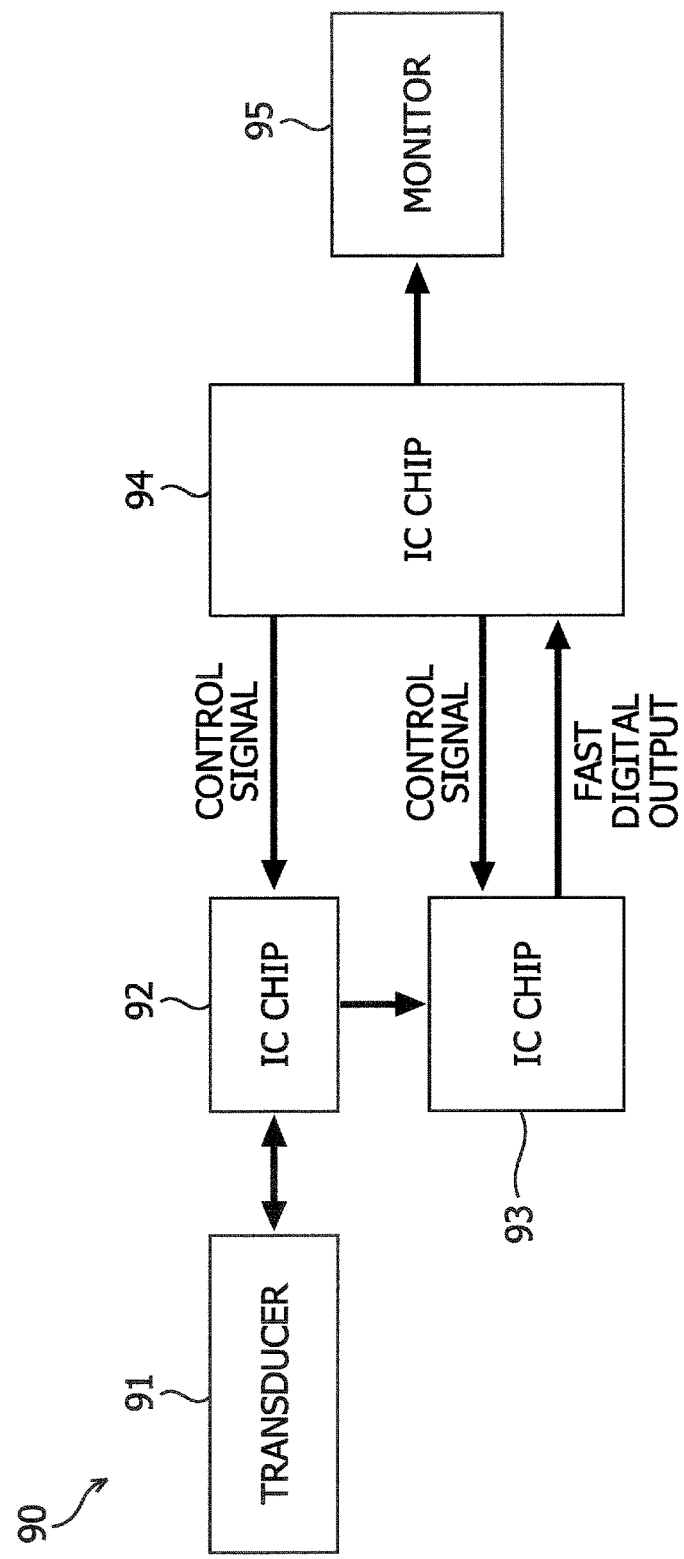
FIG. 11 is a block diagram of the ultrasonic diagnostic imaging apparatus.

FIG. 4 depicts an example of disposing four connection terminals 121 along respective two face-to-face sides of the IC chip 12. Eight connection terminals 121 may also be disposed along one side of the IC chip 12 without being limited to the example depicted in FIG. 4. FIG. 10 is a diagram illustrating one example of disposing the IC chips 11, 12 when the eight connection terminals 121 are disposed along one side of the IC chip 12. FIG. 10 perspectively illustrates, as viewed on plane, a position of disposing the IC chip 11 on the circuit board 20 and a position of disposing the IC chip 12 on the circuit board 20.

Each of the plurality of connection wires for connecting the IC chip 11 to the IC chip 12 is formed within the circuit board 20 so as not to intersect each other as viewed on the plane. Occurrence of the crosstalks in the plurality of connection wires for connecting the IC chip 11 to the IC chip 12 is thereby restrained. As illustrated in FIG. 10, the plurality of connection wires for connecting the IC chip 11 to the IC chip 12 is arranged within the circuit board 20 so as not to intersect the wires connected to the control terminals 124 of the IC chip 12 as viewed on the plane. Restrained consequently is the occurrence of the crosstalks in the connection wires for connecting the IC chip 11 to the IC chip 12 and the wires connected to the control terminals 124 of the IC chip 12. The wires connected to the control terminals 124 of the IC chip 12 are the connection wires for connecting the IC chip 12 to the IC chip 13, and are also the wires through which the control signals transmitted to the IC chip 12 from the IC chip 13 propagate.

The ultrasonic probe 2 enables the restraint of the mixing of the noises into the echo signals propagating through the connection wires for connecting the transducer 10 to the IC chip 11, and also enables the restraint of the mixing of the noises into the echo signals propagating through the connection wires for connecting the IC chip 11 to the IC chip 12. Therefore, even when transmission/reception power of the ultrasonic waves is attenuated by stepping down a pulse voltage transmitted to the transducer 10, it is feasible to restrain the noises from being mixed into the echo signals. Accordingly, the pulse voltage transmitted to the transducer 10 is enabled to be stepped down, resulting in an improvement in terms of decreasing the power consumption of the ultrasonic probe 2. The ultrasonic probe 2 enables a reduction of the area of the connection wires for connecting the IC chip 11 to the IC chip 12, resulting in a decreased packaging area of the circuit board 20 and an improvement of downsizing the ultrasonic probe 2.

What is claimed is:

1. An ultrasonic probe comprising:
    a transducer configured to transmit and receive ultrasonic waves, and convert ultrasonic signals into analog voltage signals and vice versa;
    a first IC chip configured to transmit pulse voltage signals to the transducer and receive the analog voltage signals from the transducer;
    a second IC chip configured to convert the analog voltage signals received from the first IC chip into digital values from analog values and output digital voltage signals;
    a third IC chip configured to receive the digital voltage signals from the second circuit;
    a battery unit configured to supply electric power to the first IC chip, the second IC chip and the third IC chip; and
    a substrate being provided with the transducer, the first IC chip, the second IC chip and the third IC chip, wherein
    the first IC chip is disposed on a first surface of the substrate,
    the second IC chip is disposed on a second surface opposite to the first surface of the substrate,
    the second IC chip includes a plurality of first connection terminals to which the analog voltage signals are inputted, a plurality of second connection terminals from which the digital voltage signals are outputted, a first pair of sides opposed to each other and a second pair of sides opposed to each other,
    the second pair of sides is different from the first pair of sides,
    the plurality of first connection terminals is arranged along the first pair of sides, and
    the plurality of second connection terminals is arranged along one of the second pair of sides.

2. The ultrasonic probe according to claim 1, further comprising:
    a plurality of first connection wires configured to connect the first IC chip to the second IC chip,
    each of the plurality of first connection wires being formed within the substrate so as not to intersect each other as viewed on plane.

3. The ultrasonic probe according to claim 2, further comprising:
    second connection wires configured to connect the second IC chip to the third IC chip, and
    the third IC chip being disposed on the first surface or the second surface of the substrate,
    the plurality of first connection wires and the second connection wires being formed within the substrate so as not to intersect each other as viewed on the plane.

4. The ultrasonic probe according to claim 3, further comprising:
    a first power source circuit configured to control the electric power supplied to the first IC chip and the second IC chip; and
    a second power source circuit configured to control the electric power supplied to the third IC chip.

5. The ultrasonic probe according to claim 4, wherein the first power source circuit is a DC-DC converter,
    the transducer includes oscillators, and
    a predetermined frequency including a resonance frequency of the oscillator is different from an operation frequency of the DC-DC converter.

6. The ultrasonic probe according to claim 1, further comprising:
    a second substrate being disposed in a face-to-face relationship with the substrate and being provided with the battery unit,
    the battery unit being disposed on the second substrate so as to face the first IC chip.

7. The ultrasonic probe according to claim 1, further comprising:
    a second substrate being disposed in the face-to-face relationship with the substrate and being provided with the battery unit,
    the battery unit being disposed on the second substrate so as to face the second IC chip.

8. The ultrasonic probe according to claim 1, wherein the first IC chip includes a plurality of third connection terminals, and the plurality of third connection terminals are disposed so as to surround, as viewed on the plane, the plurality of first connection terminals and the plurality of second connection terminals.

* * * * *